(12) United States Patent
Welland et al.

(10) Patent No.: US 6,972,423 B2
(45) Date of Patent: Dec. 6, 2005

(54) SENSOR

(75) Inventors: Mark E. Welland, Cambridge (GB); Trevor Rayment, Cambridge (GB)

(73) Assignee: Cambridge University Technical Services, Ltd., (GB)

( * ) Notice: Subject to any disclaimer, the term of this patent is extended or adjusted under 35 U.S.C. 154(b) by 202 days.

(21) Appl. No.: 10/360,513

(22) Filed: Feb. 6, 2003

(65) Prior Publication Data

US 2003/0222232 A1    Dec. 4, 2003

Related U.S. Application Data

(63) Continuation of application No. 09/600,728, filed as application No. PCT/GB99/00199 on Jan. 21, 1999, now abandoned.

(30) Foreign Application Priority Data

Jan. 21, 1998    (GB) .................................. 9801286

(51) Int. Cl.[7] ............................................ G01N 15/06
(52) U.S. Cl. ...................................... 250/573; 250/574
(58) Field of Search ............................. 250/573, 222.2, 250/574; 356/338, 436, 441; 435/6, 526; 436/518, 161, 524

(56) References Cited

U.S. PATENT DOCUMENTS

| | | | |
|---|---|---|---|
| 4,549,427 A | 10/1985 | Kolesar, Jr. | |
| 5,019,238 A | 5/1991 | Cormier et al. | |
| 5,445,008 A | 8/1995 | Wachter et al. | |
| 5,574,279 A | 11/1996 | Ikeda et al. | |
| 6,016,686 A | 1/2000 | Thundat | |
| 6,436,647 B1 * | 8/2002 | Quate et al. | 435/6 |

FOREIGN PATENT DOCUMENTS

EP    0703429 A2    3/1996

OTHER PUBLICATIONS

Chen, G. Y. et al. "Adsorption-induced Surface Stress and Its Effects on Resonance Frequency of Microcantilevers" *Journal of Applied Physics*, 1995, pp. 3618-3622, vol. 77, No. 8.

* cited by examiner

*Primary Examiner*—Que T. Le
(74) *Attorney, Agent, or Firm*—Saliwanchik, Lloyd & Saliwanchik

(57) ABSTRACT

The present invention pertains to a sensor, suitable for use in the detection of an analyte in a fluid, comprising: a tube (4) defining a flow path for the fluid; a generally planar member (3) mounted in the flow path (→) such that the plane is in the direction of flow, wherein the member has, bound thereto, a ligand that interacts with the analyte, wherein interaction causes the member to flex; and means (1, 2) for the detection of the flexing.

14 Claims, 4 Drawing Sheets

SENSOR

CROSS-REFERENCE TO RELATED APPLICATION

This application is a continuation of U.S. application Ser. No. 09/600,728, filed Oct. 13, 2000 now abandoned, which is the U.S. national stage of international application No. PCT/GB99/00199, filed Jan. 21, 1999.

FIELD OF THE INVENTION

This invention relates to a sensor of the type that is suitable for the detection of an analyte in a fluid. More particularly, the invention relates to a method of screening a target compound with respect to a plurality of analytes.

BACKGROUND OF THE INVENTION

Screening is of major importance in the pharmaceutical industry. For example, combinatorial chemistry may be used to generate a library containing a large number of compounds which have to be screened as potential drug candidates. Further, new drugs must be screened against the molecules they will encounter in use. The efficiency of screening is of major commercial importance, since it is a limiting step in the rate of identification and development of new drug candidates.

Currently, screening is conducted using labels such as radionuclides or fluorophors. Safety considerations are causing a move away from radionuclides. Fluorescent labels are not always suitable for use with small molecules, and their use may involve delay while the fluorescent signal develops. Conventional screening techniques may also require complicated robotics and large volumes of test liquids.

Butt has proposed that changes in surface stress on a silicon nitride surface may be measured upon gaseous silanation and upon protonation in water. This article also "discloses" the unspecific adsorption of bovine albumin protein on a thiolated surface.

SUMMARY OF THE INVENTION

The present invention is based on the direct detection of target-analyte interaction, however transitory. In a novel device according to the present invention, i.e. a sensor for use in the detection of an analyte in a fluid, its components comprise a tube defining a flow path for the fluid; a generally planar member mounted in the flow path such that the plane is in the direction of flow, wherein the member has, bound thereto, a ligand that interacts with the analyte, whereby interaction causes the member to flex; and means for the detection of the flexing.

Such a device can be used to screen a target compound with respect to a plurality of analytes, by causing the analytes to flow through the tube, the target compound being immobilised as the ligand, and detecting any flexing of the member. Such detection can be conducted simply and efficiently, with high throughput.

The sensor's basic reaction time may be about 1 msec. Several such members, each adapted to test a different drug, may be used in series. The sensor provides direct, physical measurement, without chemical reaction, and is operable with a wide range of sizes of drug molecules. Continuous flow can be used, without requiring large volumes of test fluids. Only simple electronics may be required, so that a device of the invention can be produced economically, while the small size of each planar member enables many to be used in one compact instrument.

DESCRIPTION OF THE INVENTION

By way of illustration, a microfabricated cantilever, as used in AFM, is mounted in the chosen environment and the bending of the lever is monitored using a laser deflection method. For example, a beam from the laser diode is collimated and focused onto the end of the cantilever, and the reflected light is collected by a linear position sensitive photodiode. The sensitivity of this simple arrangement is typically 100 pm (DC) or 3 pm/$\sqrt{\text{MHz}}$ (AC) of lever deflection. The cantilever surfaces can be modified by specific coatings, e.g. to enhance adsorption.

Different stresses acting on the front and back of the cantilever cause the lever to bend. For example, preferential adsorption of an analyte on one side of the cantilever means that a surface stress may be developed. Such stresses can be very large, even for submonolayer coverages, and the resulting lever deflections are easily measured. Particularly in liquid environments, it is preferable to use changes in surface stress as the measurement basis of a realistic sensor. Temperature or mass measurements can also be made.

Temperature changes (and hence also, via calorimetry relationships, heat and power changes) can be measured by coating the lever to make it a bimetallic strip. The analysis of the temperature variations across the bimetallic strip can be performed analytically or using finite element techniques. Measurement resolutions of the order of $10^{-5}$ K, 20 fJ and 10 pW can be expected from standard, metal-coated $Si_3N_4$ cantilevers. The bimetallic method can be used to study chemical reactions, optical adsorption in thin films and molecules, and phase in alkane solids.

AFM sensors can measure the mass of material adsorbed or deposited onto a lever, with a resolution of the order of 1 pg. This is generally performed in ambient or vacuum, where small mass loadings can be measured with great accuracy, from the change in the cantilever resonance frequency. Small static deflections of the lever may be more difficult to measure, above the system drift level.

Any initial drift may be considerably reduced by allowing the system to settle down, e.g. for 4 hours or more. Any drift caused by the evaporation of solvent may be prevented by obstructing the inlet and outlet of the cell before and after injection of the analyte solution.

An example of using micromechanical sensors to measure surface stress, induced by adsorption in the liquid phase, involves the response of a cantilever, coated on one surface with gold, to the formation of a self assembly monolayer (SAM) of an analyte such as thiol molecules. As another example, a cantilever can be functionalised by coupling with chemically-sensitive, e.g. pH-sensitive, colloidal macromolecules.

Proteins generally have a net charge, which is determined by the sum of the amino acid charges. Proteins can therefore undergo electrostatic interactions with a charged surface, although the latter are relatively short-range forces, because of the screening of charges by the aqueous environment. However, if an electrostatic interaction does occur, the charge coupling may change the surface stress due to a redistribution of the local electronic environment, as for chemisorption.

Charge-transfer interactions between electron-donating and electron-accepting species are also important in adsorption processes on solid surfaces. Hydrogen bonding is an example of a strong charge-transfer interaction in which the positive charge of the hydrogen proton is donated to a suitable acceptor. Changes in surface stress may be induced by this type of interaction, again as a result of the implicit rearrangement of the surface charge distribution.

Another significant component responsible for protein adsorption is the hydrophobic interaction, which is the unusually strong attraction between hydrophobic molecules (or portion of molecules) and surfaces in water. There is no bond associated with this mainly entropic phenomenon which arises from the tendency to minimise the interfacial areas between water and non-polar solutes or surfaces, i.e. to minimise the surface free energy. According to Shuttleworth's equation, a change in surface stress should result from this phenomenon, and may be strongly dependent on the size of the hydrophobic domains interacting.

Adsorbent surfaces such as Au, Si and $Si_3N_4$ are reactive when clean. Therefore, they are likely to become contaminated when in contact with an environment other than vacuum. Their hydrophilic properties while clean therefore disappear to leave surfaces which are mainly hydrophobic. This indicates that hydrophobic interactions are very likely to happen, between proteins and the cantilever surfaces.

Test injections of dye in a cell have suggested that the adsorbate sample should be injected as close as possible to the cantilever. A more systematic method of injection may be adopted, by injecting slowly as close as possible to the cantilever with a long needle syringe. For example, thiol in ethanol diffused around the cantilever quickly and the reproducibility of the kinetics was improved. Alternatively, a flow cell arrangement may be suitable, especially when large adsorbate samples are available.

It may be noted that ethanol is a good solvent for thiols, and the tail of the adsorbed molecule can extend in the surrounding liquid. Thus, higher packing densities may be achieved more readily because of increased molecular mobility. Alternatively, the solvent itself, which resides between the thiol chains, may give rise to additional lateral forces to push the chains apart.

It is preferred to functionalise both surfaces of the cantilever. For example, a method for depositing PEG, to make one surface inert, has been demonstrated. The possibility of functionalising the cantilever sensor with chemically-sensitive gel macromolecules has also been investigated. pH-sensitive microgel particles have been successfully deposited on the cantilever. The pH-dependent variation of their volume induced a change in the cantilever surface stress, hence in the deflection of the cantilever.

Studies on protein adsorption have demonstrated that SAMs formed by the chemisorption of oligo(ethylene oxide)-terminated alkanethiol impedes the adsorption of a large range of proteins. Therefore, functionalising the second surface with that particular thiol should be an effective way to make it passive to protein adsorption processes. 1 mM $HS(CH_2)_{10}(CO_2C)_2COCH_3$ solution (referred to below as "PEG-thiol") has been used for this purpose.

It is also possible to functionalise a surface by coating with a gel. Some microgel particles are known to exhibit rapid volume changes under different chemical conditions, due to the electrostatic interactions between internal chemical groups. For example, the hydrodynamic diameter of anionic microgel particles increases under alkaline conditions and decreases under acidic conditions. In the case of acrylic acid microgel particles, the electrostatic repulsion between the internal dissociated carboxyl groups in a basic environment may cause the particles to swell and the swelling consequently decreases if these chemical groups become associated with protons in an acid environment.

Various features of the invention will be evident from the following description, in which the accompanying drawings are used to illustrate the invention. In the drawings.

Figure 1:
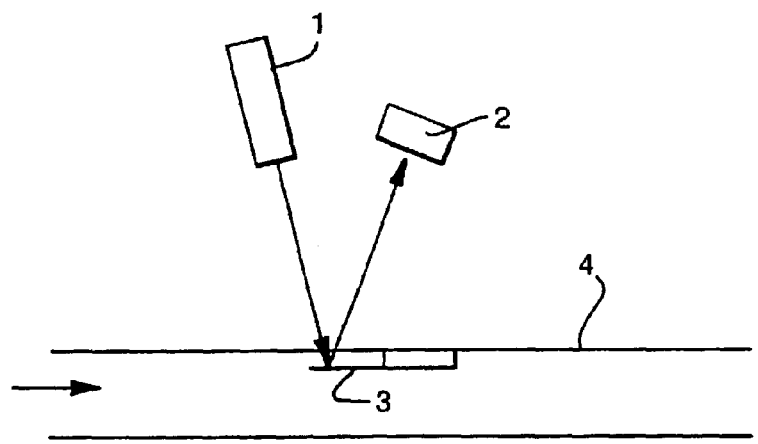
FIG. 1 is a schematic illustration of a device embodying the present invention.

Referring first to FIG. 1, as the most simple representation of the invention, the detection means comprises a laser diode 1, and a photodiode 2 which receives information by reflection from a planar member 3. The planar member 3 acts as a cantilever, and is mounted within a tube 4 defining fluid flow. The direction of flow is indicated by a thick arrow. The face of the member that receives the laser irradiation is suitably coated with a reflective material such as gold. The opposite face has a ligand or target compound immobilised thereon, by conventional means. The mounting may also be achieved by conventional means.

By way of example, the sensor member comprises a commercially-available, silicon nitride cantilever for an AFM, measuring about 100×20 $\mu$m. It may be produced by photolithography; wet anistropic etching provides a desired thickness, e.g. 0.1 $\mu$m. A thin layer of gold is evaporated onto one surface. A target compound is immobilised on the opposite face.

In use, the coated sensor is then placed in a small fluid reaction chamber and the test solution pumped through. If molecules in the test solution bind to the target compound, a surface stress is induced in the cantilever whose tip then moves up or down. This movement can be accurately and easily detected by directing light from the laser diode, a commercially-available CD component, through a window in the fluid test cell, onto the cantilever tip. The reflected light is detected by the photodiode.

Figure 3:
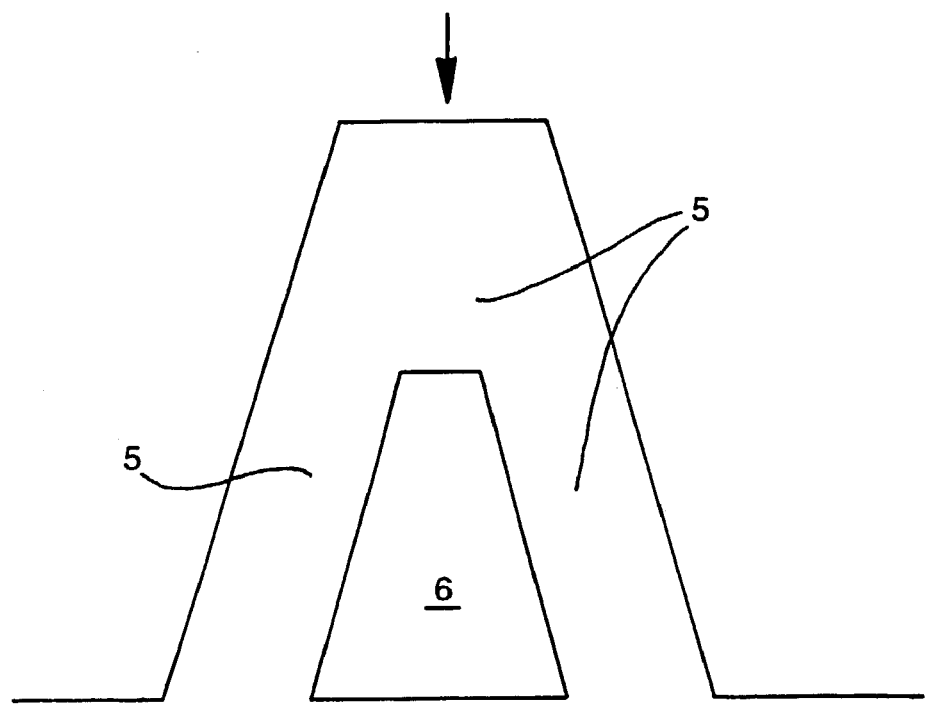
FIGS. 3 and 4 are plan views of planar members that can be used in embodiments of the invention.

A suitable sensor member is shown in plan, in FIG. 3, and comprises coated areas 5. The sensor member includes an aperture 6, to increase its torsional rigidity.

Figure 4:
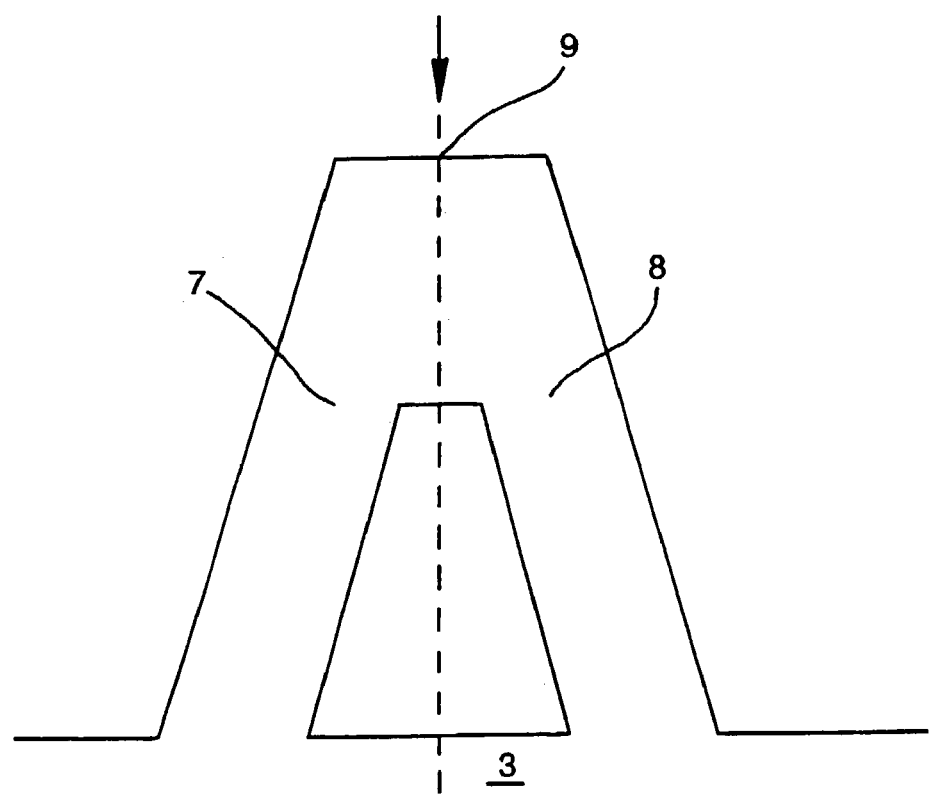

A preferred sensor member is shown in FIG. 4, where the target drug or other test compound and also a reference compound are provided in discrete areas, respectively indicated as 7 and 8. These areas are separated by the dotted line. Interaction between an analyte and the target compound causes the tip 9 of the sensor member 3 to rotate about the axis defined by the dotted line. Rotation is easily distinguishable from up-and-down movement caused by drift. Any interaction with the reference compound, defining background or common mode noise, can be distinguished and rejected. The twisting movement can be detected simply, using a quadrant photo diode detector. Other means of detecting the twisting movement will be apparent to those skilled in the art and include resistive strain gauges or piezo-electric elements incorporated into the cantilever. Particularly in connection with the use of this embodiment, it may be desirable to control the conditions, e.g. temperature.

Figure 2:
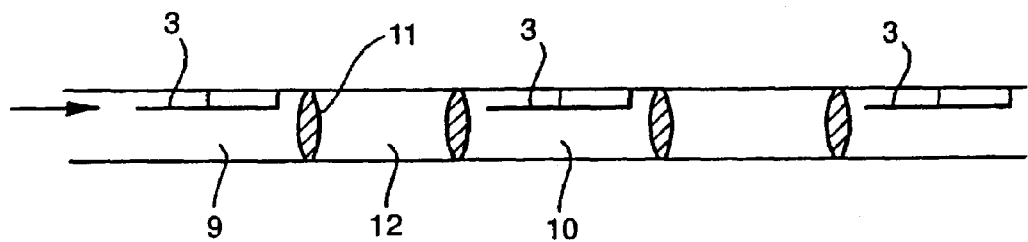
FIG. 2 is a schematic view of part of a further embodiment of the invention.

The present invention is particularly suited to the rapid testing of a target compound with many different analytes, supplied sequentially. FIG. 2 shows multiple sensors for this purpose, e.g. the detection of any interaction between a number of naturally-occurring molecules and different target compounds immobilised on each sensor member. The respective test fluids (two of which are indicated specifically, by reference numerals 9 and 10, in FIG. 2) are conveniently separated by gas microbubbles 11 whose presence can be used for the purposes of calibrating the device. A further advantage of this system is also shown in FIG. 2, i.e. the provision of flushing fluid at 12, between respective units of test fluid.

Figure 5:
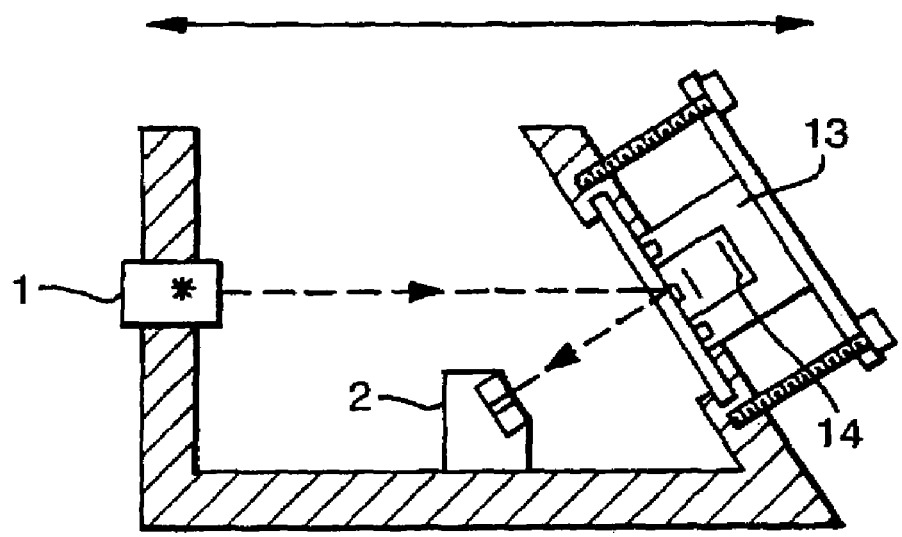
FIG. 5 is a schematic view of a liquid cell and apparatus for use in the invention.
Figure 6:
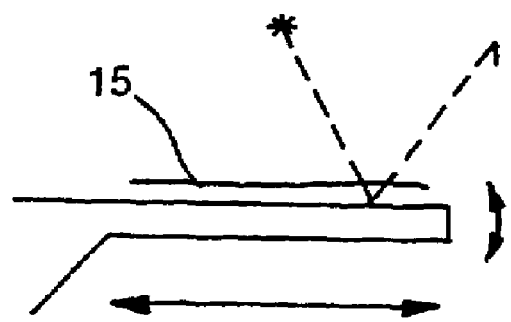
FIG. 6 shows a cantilever that may be used in the invention, in more detail.

FIGS. 5 and 6 show a liquid cell 13 (e.g. of PTFE) including electrodes 14 and a cantilever having a modified surface 15, in more detail. The cantilever is mechanically rigid and easily adapted for a variety of liquid cells and electrochemical electrodes. Typically, the dimensions shown by the double-headed arrows on straight lines, in FIGS. 5 and 6, are 60 mm and 100 $\mu$m, respectively. The curved double-headed arrow, in FIG. 6, indicates the bending of the lever.

The following Examples illustrate the invention.

EXAMPLE 1

This Example illustrates the preparation of a cantilever.

One surface of $Si_3N_4$ cantilevers is generally coated by the manufacturer with a thin layer of gold, to improve their reflectivity for AFM applications. A thin layer of chrome is usually deposited beforehand, to improve the adhesion of the gold layer on the cantilever, especially for work in liquid where gold on its own tends to peel from the silicon nitride. Before any experiment involving adsorption in liquid, the existing metal layers were removed by the immersion of the cantilevers for about 20 s in aqua regia (3 parts HCl, 1 part $HNO_3$, 1 part $H_2O$) then for about 20 s in chrome etchant. The cantilevers were then rinsed in deionised water and dried with nitrogen. Any subsequent evaporation of gold generally includes a prior deposition of 10 Å (1 nm) of chrome, especially if the cantilevers are incubated afterwards in a thiol solution. 200 $\mu$m long V-shaped cantilevers, 0.5 $\mu$m thick and 40 $\mu$m wide (the width of each leg of the V) was coated with a film of gold and used in the following Examples.

EXAMPLE 2

The adsorption of alkylthiols on a gold surface was investigated. The cantilever was coated with 25 nm of gold deposited by thermal evaporation.

The cantilever was immersed in a static fluid cell, volume 2 $cm^3$, constructed from PTFE and filled with ethanol. The cantilever was fixed to a glass window which formed one wall of the cell. Motion of the cantilever was detected by measuring the change in angle of reflection of a solid-state laser beam focused onto the back of the cantilever through the glass window. The position of the reflected beam was detected with a quadrant photodiode.

Figure 7:
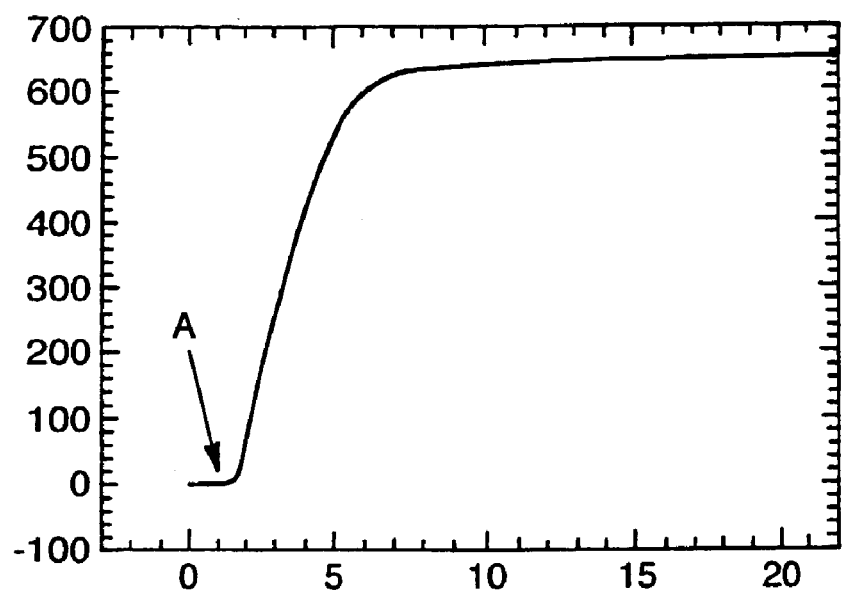
FIG. 7 is a graph showing the progress of the deflection (nm) of a gold-coated micromechanical cantilever arising from the adsorption of low density lipoprotein, against time.

$C_{12}H_{26}S$ was injected into the fluid cell with a hypodermic at a concentration of 10 mM. The adsorption of the alkylthiol onto the surface effected motion of the cantilever as a result of compressive surface stress induced. The resultant curve of deflection versus time (FIG. 7) shows an instantaneous response as the alkylthiol, administered at time point A, rearranges itself on the cantilever to lower its surface energy, and also the stability of the response over minutes.

EXAMPLE 3

The gold and chromium films present on the commercial cantilevers were etched using the method described in Example 1. Then, 300 Å of gold was evaporated on the top surface of the cantilever at a pressure of $10^{-6}$ mbar at room temperature. This was the only step performed to functionalise the cantilever surface, to test the adsorption of LDL on gold.

Figure 8:
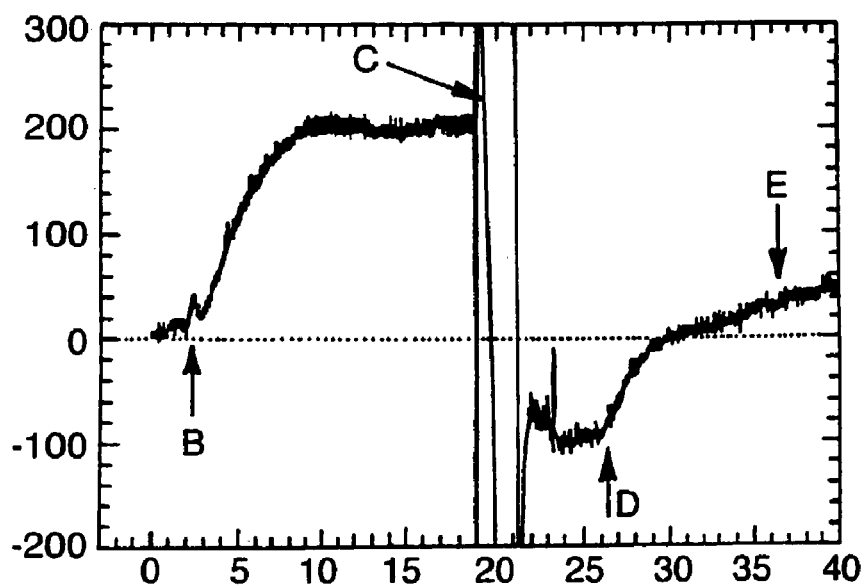
FIG. 8 is a graph showing cantilever deflection (nm) for adsorption of SAM $C_{12}H_{25}SH$ onto gold in an ethanol solution, against time (min).

FIG. 8 shows the results, using LDL. LDL is introduced at time point B and again at point D. At point C, the cell is flushed with ethanol and then buffer. The region indicated by point E shows thermal drift.

EXAMPLE 4

Following treatment as in Example 1, and coating with gold, the cantilever was incubated in a solution of 2-aminoethanethiol hydrochloride ($H_2NCH_2CH_2SH.HCl$, Aldrich) in an ethanol-water solution at a concentration of 0.5 mg/ml for a minimum of 6 hours. After being rinsed thoroughly in ethanol and then in ultra high purified (UHP) water and dried with nitrogen, the cantilever was left for 20 min in a 1.5 mg/ml aqueous solution of heparin (from bovine intestinal mucosa, Sigma). The —COOH group of heparin interacts with the —$NH_2$ terminal group of the thiol to form a peptide covalent bond. The cantilever was then rinsed in water. The coverage of heparin on the thiol surface is low (maximum 10%). To avoid unspecific binding of LDL/oxLDL on gold or on the free —$NH_2$ groups, the cantilever was then incubated in a 2 mg/ml Bovine Serum Albumin (BSA) solution in buffer (50 mM phosphate buffer with 0.15M NaCl, pH=7.4) for 10 min. BSA is often used as a blocking agent of non-specific binding sites. SPR measurements confirmed its effectiveness, indicating that the surface coverage of LDL on a BSA modified surface is only 3% of the surface coverage on an unmodified gold surface. The cantilever was rinsed in buffer and then mounted in a 0.3 ml liquid PTFE cell filled with buffer.

In order to measure the surface stress resulting from the binding of the lipoproteins on a cantilever surface, the second surface of the cantilever made inert, as discussed above. This means that the biological substances to be detected should be inhibited from binding on this surface, and this may be done by functionalising it by using a PEG-thiol SAM as discussed above. Each cantilever was allowed to equilibrate in buffer for about 1 to 6 hours, by which time drift was reduced to typically 20 nm/h.

LDL was isolated from fresh human plasma. Oxidation of the LDL was performed by contact with cupric sulphate ($CuSO_4$). The lipoproteins were then stored at 4° C.

Injections of LDL/oxLDL were performed using a high precision 10 ml Hamilton syringe. The syringe was cleaned with ethanol and UHP water before any injection. The response of the cantilever to the injection was recorded at a sampling interval of 0.5 s.

After each experiment, the glass disc holding the cantilever and the PTFE cell were thoroughly cleaned with acetone, isopropanol and deionised water. Then, after drying with nitrogen, a 2 minute oxygen plasma treatment was used to remove any remaining organic material.

The injection consisted of 10 ml of 3.5 mg/ml LDL. The most obvious feature of the response is that it can be divided into two parts: a rapid process for the first 3 min after the injection followed by a slower process generally reaching equilibrium after 40 min. The first part can be explained as the rapid adsorption of the lipoproteins on the gold surface.

The direction of the cantilever bending corresponds to compressive surface stress. The second part of the curve (downwards) can be interpreted as the interaction of the LDL with both surfaces, gold and silicon nitride. This interaction was probably due to a gradual rearrangement of the molecules on the surfaces. This feature was even more pronounced in some of the other experimental runs, and the total amplitude of this effect can be up to twice the amplitude of the first, quick adsorption process.

LDL can in principle be removed from the gold surface by rinsing the cantilever in ethanol as the lipids get dissolved by contact with alcohols. After the initial injection of LDL, the PTFE cell was filled with ethanol for 1 min, and then rinsed thoroughly with buffer (with at least 10 times the quantity of ethanol). The cantilever was then allowed to equilibrate from the perturbations induced by the rinse. A subsequent injection of LDL triggered a different response compared to the initial injection. The amplitude of the response is smaller than on the fresh gold and can be explained by the fact that the rinsed gold was not as lipoprotein-free as the initial gold surface since some lipoproteins may not have been removed by the ethanol rinse. The surface coverage induced by the injection would be therefore smaller, hence the surface stress would be smaller. This is also consistent with the fact that the kinetics of the responses are also different: the response is much slower on rinsed gold than on fresh gold. In addition, the downward second part apparent initially is not present after the rinse. This feature was highly reproducible.

When choosing heparin as a ligand for LDL, the electrostatic interaction occurring between the two species is inhibited in the presence of a sufficient amount of NaCl which acts as an ionic shield to the former interaction. In order to detach the LDL from the surface, the liquid cell was filled with a solution of 0.5M NaCl for 1 min, then approximately 5 ml of buffer was passed through the cell to remove any trace of NaCl. When the cantilever deflection reached equilibrium, a new injection of LDL was performed.

The same experiments were performed with oxLDL at a concentration of 0.3 mg/ml. The response of the cantilever over 70 min to a 10 ml injection of oxLDL, and its response to the same quantity injection of LDL but of concentration 3.5 mg/ml, are completely different in shape. The change in surface stress triggered by the presence of oxLDL is tensile for the first minute then compressive until the response seems to stabilise after 70 min. In terms of magnitude, the total surface stress induced in the whole process is very large (0.07 $Nm^{-1}$) considering the low concentration of oxLDL.

Accordingly, the possibility of detecting the difference between LDL and oxLDL with a surface stress based microsensor was demonstrated. A small alteration in the LDL/OxLDL composition or morphology may change the particle-surface interactions. These results demonstrate the possibility of using the sensor to monitor rearrangements of molecules involving stress, which is an advantage over other existing methods for the detection of the adsorption of bio-species.

EXAMPLE 5

The use of gel materials to functionalise microcantilever-based sensors is demonstrated in this Example, using 5% acrylic acid-poly(N-isopropylacrylamide). The cantilever itself was made insensitive to pH changes by evaporating a 250 Å gold film on both surfaces of the cantilever. This is necessary because a $Si_3N_4$/Au cantilever is sensitive to pH variations arising from the reactivity of the $Si_3N_4$ exposed surface groups (SiOH, $SiO^-$ and $SiNH_2$) with protons. A surface stress as large as 5 mN per unit pH was measured. A layer of particles was deposited on the cantilever top Au surface with the help of dental floss. The layer could be observed with an optical microscope since the diameter of the particles in neutral pH solution is about 900 nm. The adhesion of particles was strong enough so that rinsing the cantilever with acidic and alkaline solutions did not seem to alter the layer. SEM pictures of the corresponding surface showed that the particles were not interconnected, which suggests that any detected cantilever movement would be due to the volume change of individual particles and not to an expansion or contraction between particles.

The functionalised cantilever was placed in a 2 ml measuring cell. A flow cell arrangement was used for this experiment. The fluid could be pumped through a 3-way valve system from either of two reservoir flasks containing a $HNO_3$ solution at pH 3.5 and a KOH solution at pH 9 respectively. The flow speed was limited to 0.5 ml/s to avoid mechanical perturbation of the cantilever.

The $HNO_3$ solution was passed through and the system allowed to equilibrate. The particles were likely to dry after deposition, and were therefore expected to swell when in contact with liquid. The direction of the drift was indeed consistent with particle swelling inducing a compressive surface stress change. Once equilibrium was reached, the pH was cyclically varied from 3.5 to 9.

When the pH was increased from 3.5 to 9, the direction of the cantilever bending was consistent with a compressive stress change resulting from the swelling of the particle. The striking feature was the reproducibility of each cycle, showing a rapid change which is likely to correspond to the swelling transition occurring between pH 4 and 6 observed with Photo Correlation Spectroscopy (PCS). PCS measurements indicate a change in the hydrodynamic diameter of 200 nm for particles in solution which should be less for particles adhered on a surface because the particles are constrained. The measured deflection of the cantilever in the swelling transition was only 160 nm, which corresponds to a much smaller expansion of the surface than expected if the swelling gel particles were mechanically interconnected forming a more homogeneous layer. This supports the idea that the particles deposited on the cantilever contribute individually to its deflection.

We claim:

1. A sensor for use in the detection of an analyte in a fluid, the sensor comprising:
   a tube defining a flow path for the fluid;
   a generally planar member having opposed faces mounted in the flow path such that the plane is in the direction of flow, wherein the member has, bound thereto, in separate areas, a ligand and a reference compound, wherein the ligand interacts with the analyte, and wherein the interaction causes different stresses to act on the opposed faces of the member, thereby causing the member to flex;
   means for the detection of the flexing; and
   means for distinguishing between the ligand signal and the reference compound signal, whereby common mode noise can be determined.

2. The sensor according to claim 1, wherein the ligand is bound to one face of the member, and the other face is coated with a material that is responsive to the detection means.

3. The sensor according to claim 2, wherein the detection means comprises a laser.

4. The sensor according to claim 1, wherein the detection means comprises a laser.

5. The sensor according to claim 1, wherein the member includes an aperture, whereby its torsional rigidity is increased.

6. The sensor according to claim 1, which comprises a plurality of the members, positioned in series, having respective ligands bound thereto.

7. The sensor according to claim 1, wherein the fluid is a liquid.

8. A method for screening a target compound with respect to a plurality of analytes in a fluid, which comprises:
   causing the analytes to flow through the tube of a sensor, wherein the sensor comprises a tube defining a flow path for the fluid; a generally planar member having opposed faces mounted in the flow path such that the plane is in the direction of flow, wherein the member has, bound thereto, in separate areas, a ligand and a reference compound, the target compound being the ligand, wherein the ligand interacts with the analyte, and wherein the interaction causes different stresses to act on the opposed faces of the member, thereby causing the member to flex; means for the detection of the flexing; and means for distinguishing between the ligand signal and the reference compound signal, whereby common mode noise can be determined; and detecting any flexing of the member.

9. The method according to claim 8, wherein the analytes are provided successively, in liquid form, and bubbles are introduced between each liquid analyte, thereby allowing calibration of the device and optionally also flushing liquid between analytes.

10. The method according to claim 8, wherein the fluid is a liquid.

11. The method according to claim 8, wherein the ligand is bound to one face of the member of the sensor, and the other face is coated with a material that is responsive to the detection means.

12. The method according to claim 8, wherein the detection means of the sensor comprises a laser.

13. The method according to claim 8, wherein the member of the sensor includes an aperture, whereby its torsional rigidity is increased.

14. The method according to claim 8, wherein the sensor comprises a plurality of the members, positioned in series, having respective ligands bound thereto.

* * * * *